US00PP19063P2

(12) United States Plant Patent

Van Blokland

(10) Patent No.: US PP19,063 P2

(45) Date of Patent: Aug. 5, 2008

(54) *SEDUM* PLANT NAMED 'DIAMOND EDGE'

(50) Latin Name: ***Sedum* hybrid**
Varietal Denomination: Diamond Edge

(75) Inventor: Robbert Gijsbertus Cornelis Van Blokland, AJ De Hoef (NL)

(73) Assignee: Inspiration Plant, De Hoef (NL)

( * ) Notice: Subject to any disclaimer, the term of this patent is extended or adjusted under 35 U.S.C. 154(b) by 0 days.

(21) Appl. No.: 11/504,959

(22) Filed: Aug. 16, 2006

(51) Int. Cl.
*A01H 5/00* (2006.01)

(52) U.S. Cl. ..... Plt./479; Plt./479

(58) Field of Classification Search ..... Plt./263
See application file for complete search history.

*Primary Examiner*—Kent Bell
(74) *Attorney, Agent, or Firm*—Jondle & Associates, P.C.

(57) ABSTRACT

A new *Sedum* plant particularly distinguished by greenish-yellow variegated foliage, is disclosed.

2 Drawing Sheets

Genus and species: *Sedum* hybrid.
Variety denomination: 'Diamond Edge'.

BACKGROUND OF THE NEW PLANT

The present invention comprises a new and distinct cultivar of *Sedum,* botanically known as *Sedum* hybrid, and hereinafter referred to by the cultivar name 'Diamond Edge'. The new cultivar originated as a naturally occurring mutation in the *Sedum* plant 'Matrona' (unpatented) found in 2001 in a nursery in Zwaanshoek, The Netherlands. *Sedum* 'Matrona' is a hybrid between *S. spectabile* and *S. telephium* 'Atropurpureum'.

The new cultivar was created in 2001 in Zwaanshoek, The Netherlands and has been asexually reproduced repeatedly by vegetative cuttings and tissue culture in Zwaanshoek, The Netherlands over a four-year period. The present invention has been found to retain its distinctive characteristics through successive asexual propagations.

Plant Breeder's Rights for this cultivar were applied for with the European Union on Apr. 3, 2006.

SUMMARY OF THE INVENTION

The most outstanding and distinguishing characteristic of this new cultivar when grown under normal horticultural practices in Zwaanshoek, The Netherlands is greenish-yellow variegated foliage.

DESCRIPTION OF PHOTOGRAPHS

This new *Sedum* plant is illustrated by the accompanying photographs which show overall foliage of the plant; the colors shown are as true as can be reasonably obtained by conventional photographic procedures. The photographs are of two-year-old plants grown outside in De Hoef, The Netherlands in June 2006.

DESCRIPTION OF THE NEW CULTIVAR

Figure 1:
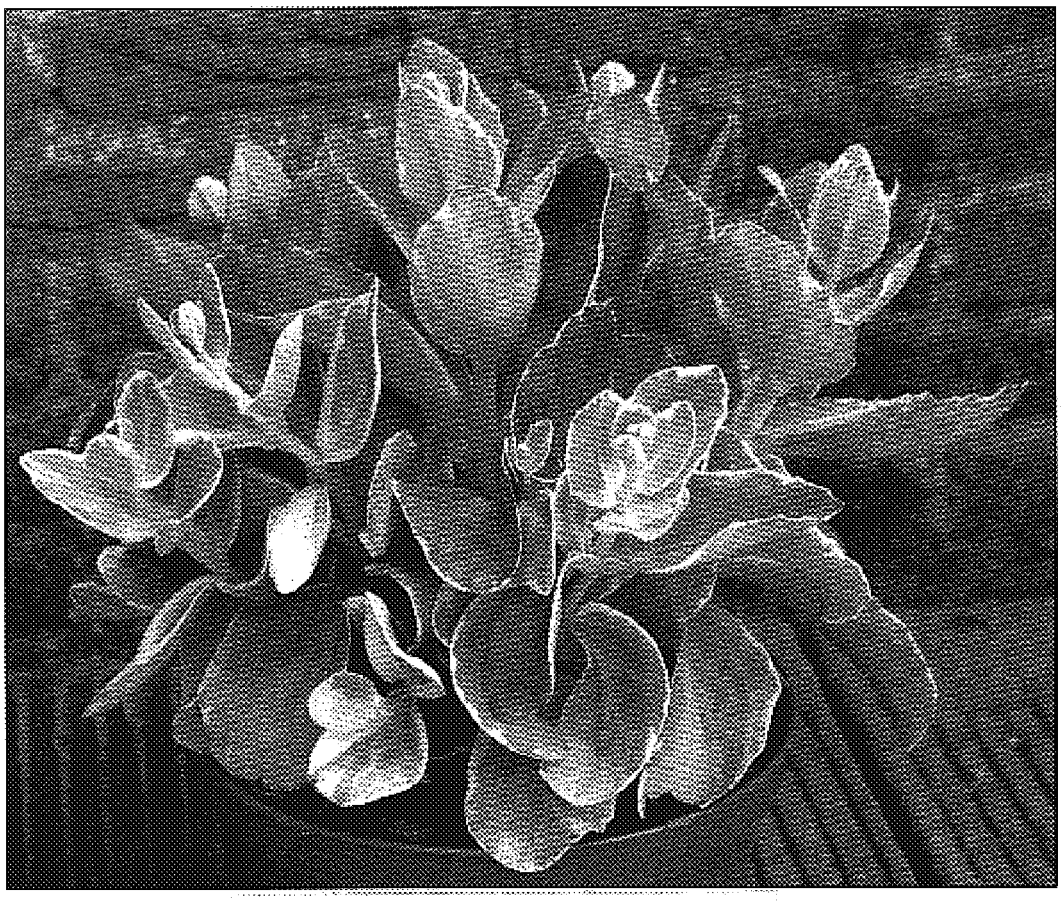
FIG. 1 shows the overall foliage.
Figure 2:
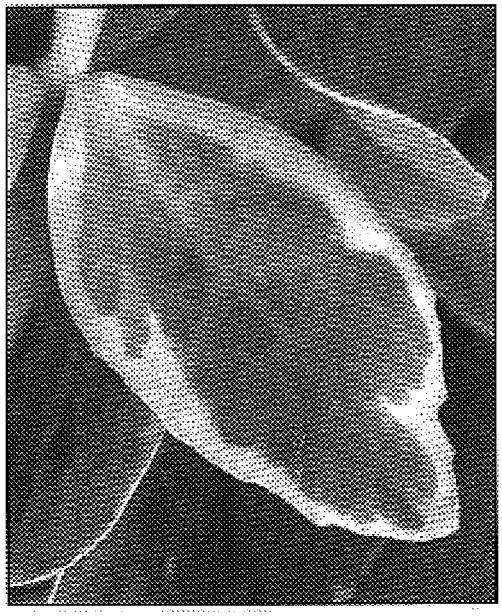
FIG. 2 shows a leaf.
Figure 3:
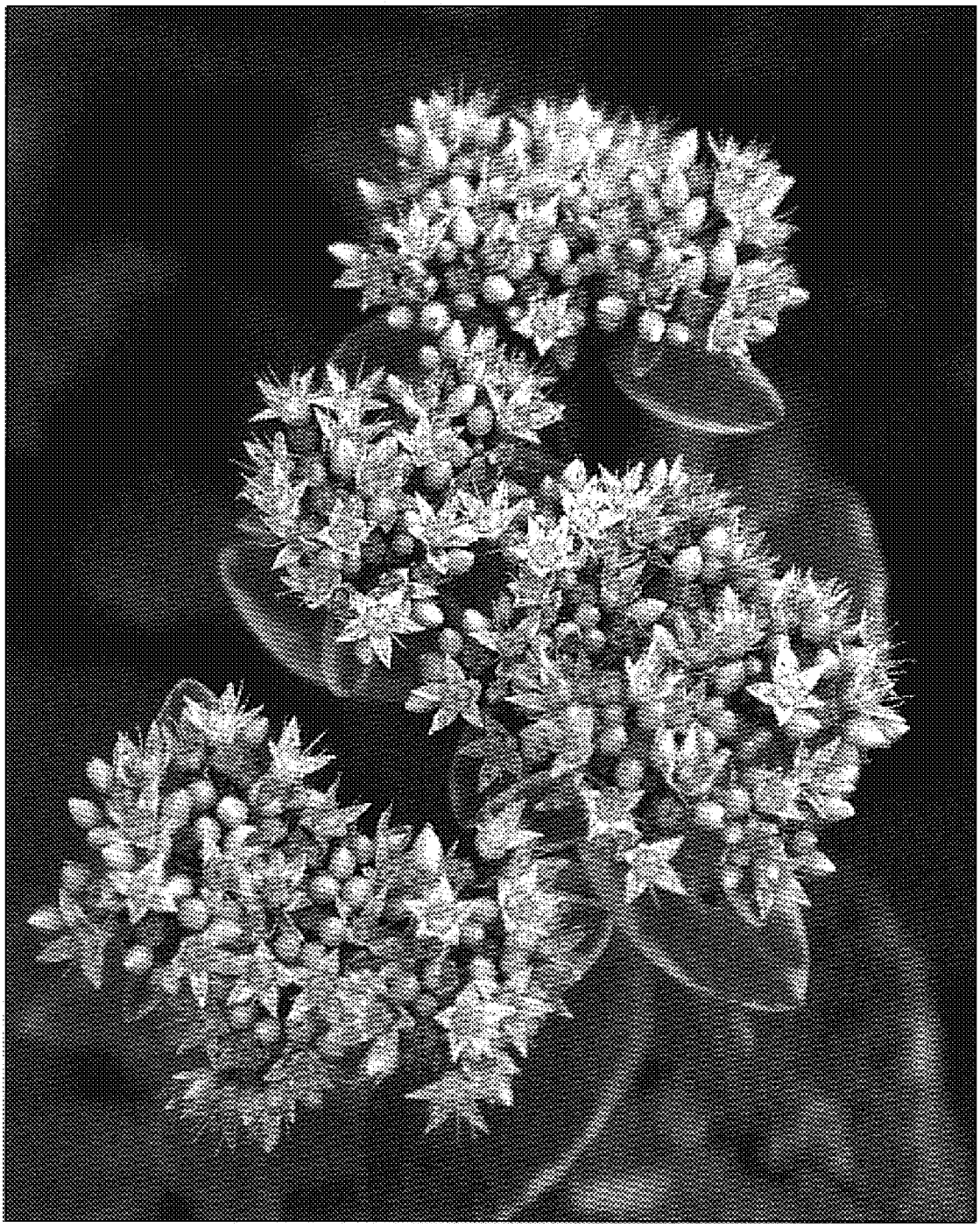
FIG. 3 shows the inflorescences of the plant.

The following detailed description sets forth the distinctive characteristics of 'Diamond Edge'. The data which define these characteristics were collected from asexual reproductions carried out in De Hoef, The Netherlands. The plant history was taken partly on two-year old plants, in June 2006. Rooted cuttings were planted in 23-cm pots and grown outdoors in De Hoef, The Netherlands. Color readings were taken under natural light. Color references are primarily to the R.H.S. Colour Chart of The Royal Horticultural Society of London (R.H.S.) (2001).

DETAILED BOTANICAL DESCRIPTION

Classification:
- *Family.*—Crassulaceae.
- *Botanical.*—*Sedum.*
- *Common name.*—*Sedum.*

Parentage: The new cultivar originated as a naturally occurring mutation in the proprietary *Sedum* plant 'Matrona' (unpatented).

Growth:
- *Form.*—Upright.
- *Height* (*measured from the top of the soil*).—24 cm.
- *Width.*—36.5 cm.
- *Propagation.*—Terminal tips for cutting.
- *Time to produce a finished flowering plant.*—24 weeks for field grown.
- *Time to initiate and develop roots* (*March/April*).—40 days.

*Root description.*—RHS 155A (white), not very dense, slightly fibrous.

Leaves:
- *Arrangement.*—Opposite.
- *Immature leaf.*—Color: Upper surface: RHS 137A and RHS 137B (green). Margin (0.4 cm): RHS 151C and RHS 151D (yellow-green). Top: Darker, RHS 153D. Base: Greener, RHS 145A to RHS 145B. Lower surface: RHS 191A to RHS 191B (greyed-green). Margin (0.4 cm): RHS 151D (yellow-green). Top: Darker, RHS 153D. Base: Greener, RHS 145A to RHS 145B. Length: 4.1 cm. Width: 2.6 cm.

*Mature leaf.*—Color: Upper surface: RHS 137B (green). Margins (0.3 cm): RHS 151B to RHS 151C (yellow-green). Top : Darker, RHS 153C to RHS 153D, slightly tinged RHS 183B to RHS 183C (greyed-red). Base: RHS 137B to RHS 137C. Lower surface: RHS 191B (greyed-green). Margins (0.3 cm): RHS 151D (yellow-green), slightly tinged RHS 183B to RHS 183C (greyed-red). Length: 11.7 cm. Width: 7.7 cm.

*Apex description.*—Bluntly acute to rounded.

*Base description.*—Cuneate.

*Shape.*—Obovate to broadly obovate, slightly curved and carinate.

*Margin.*—Irregularly dentate. Teeth per cm: 1.5 teeth. Length of teeth: 0.2 cm.

*Texture.*—Upper surface: Smooth, only slightly glossy. Lower surface: Smooth, only slightly glossy.

*Venation pattern.*—Pinnate.

*Venation color.*—RHS 183A to RHS 183B (greyed-red), RHS 145B to RHS 145C (yellow-green) towards the base.

Leaf buds:

*Length.*—0.4 cm.

*Diameter.*—0.22 cm.

*Shape.*—Oblong.

*Color.*—RHS 145A to RHS 145B (yellow-green); tipped RHS 183D (greyed-red).

*Texture.*—Smooth, dull.

Stems:

*Length.*—21.9 cm.

*Internode length.*—2.9 cm.

*Color.*—RHS 144A. to RHS 144B (yellow-green); lighter RHS 145C to RHS 145D towards the top, usually with a narrow (0.03 cm) RHS 183C to RHS 183D (greyed-purple) stripe.

*Texture.*—Smooth, dull.

Flower buds:

*Length.*—0.5 cm.

*Diameter.*—0.3 cm.

*Shape.*—Ovate.

*Color.*—RHS 147D (yellow-green); base is RHS 147A (darker yellow-green).

Inflorescence:

*Type.*—An umbel composed of an average of 150 flowers.

*Umbel diameter.*—8.9 cm.

*Umbel depth* (*height*).—7.6 cm.

*Umbel shape.*—Flattened globular.

*Flower shape.*—Single, rotate, slightly cup-shaped.

*Flower aspect.*—Upright to slightly outward.

*Blooming habit* (*flowering season*).—Late summer (mid-August to late September).

*Lastingness of flowers on the plant.*—3 weeks.

*Fragrance.*—Faint, dull and slightly musky.

*Peduncle.*—Length: 6.3 cm. Diameter: 0.3 cm. Texture: Smooth, dull. Angle relative to stem: Straight upright (average angle: 0 degrees). Color: RHS 148A to RHS 148B (yellow-green).

*Pedicel.*—Length: 0.2 cm. Diameter: 0.1 cm. Texture: Smooth, dull. Pedicle angle relative to peduncle (average angle): 20 degrees (0 degrees equal straight upright). Color: RHS 191A to RHS 191B (greyed-green) to RHS 148C (yellow-green).

Petals:

*Arrangement.*—Rotate.

*Number.*—5.

*Length.*—0.4 cm.

*Width.*—0.2 cm.

*Shape.*—Ovate.

*Apex.*—Acute.

*Base.*—Cuneate.

*Margin.*—Entire.

*Texture* (*both surfaces*).—Smooth, dull.

*Color.*—Upper surface: RHS 76D (purple) and lighter. Lower surface: RHS 144D (yellow-green) with margins that are RHS N155C (white).

Sepals:

*Arrangement.*—Campanulate; lower 50% fused.

*Number.*—5.

*Length.*—0.2 cm.

*Width.*—0.1 cm.

*Shape.*—Fused into a campanulate shape; lower 50% fused; upper (free) parts are board ovate.

*Apex.*—Acute.

*Texture* (*both surface*).—Smooth, dull.

*Color* (*both surfaces*).—RHS 191A to RHS 191B (greyed-green) to RHS 148C (yellow-green).

Reproductive Organs:

*Stamen number.*—10.

*Filament color.*—RHS 65D to RHS 155A (Red-purple to white).

*Anther.*—Shape: Ovate. Color: RHS 187C (greyed-purple). Length: 0.1 cm. Diameter: 0.05 cm.

*Ovules.*—Shape: Ovate, tapering toward the top. Length: 0.4 cm. Width: 0.2 cm. Texture: Smooth, dull. Color: RHS 157A (Green-white).

*Pollen.*—Amount: Very sparse. Color: RHS 199D (grey-brown) and lighter.

*Pistils.*—Number: 5. Length: 0.4 cm. Diameter: 0.1 cm. Stigma: Color: RHS 145C (yellow-green). Shape: Pointed. Length: 0.02 cm. Diameter: 0.02 cm. Style: Color: RHS 145B (yellow-green) flushed with RHS 63C to RHS 63D (red-purple). Length: 0.38 cm. Diameter: 0.1 cm. Shape: Ovate.

Fruit and Seed Set: None observed.

Disease and insect resistance: No special observations made.

COMPARISON WITH PARENTAL AND COMMERCIAL CULTIVARS

'Diamond Edge' differs from its parent, 'Matrona' (unpatented) by having greenish-yellow variegated foliage, whereas 'Matrona' has entirely red to brownish green leaves.

'Diamond Edge' differs from 'Frosty Morn' (unpatented) by having greenish-yellow variegated foliage, while 'Frosty Morn' has white variegated foliage. In addition, 'Diamond Edge' is more stable in its variegation than 'Frosty Morn', which easily reverts.

I claim:

1. A new and distinct cultivar of *Sedum* plant as shown and described herein.

* * * * *